(12) United States Patent
Cho (10) Patent No.: US 8,491,301 B2
(45) Date of Patent: Jul. 23, 2013

(54) GUIDE BLOCK FOR A DENTAL IMPLANT PROCEDURE AND GUIDE BLOCK ASSEMBLY, AND IMPLANT PROCEDURAL TECHNIQUE USING SAME

(75) Inventor: Sang Choon Cho, New York, NY (US)

(73) Assignee: EBI Co., Ltd. (KR)

( * ) Notice: Subject to any disclaimer, the term of this patent is extended or adjusted under 35 U.S.C. 154(b) by 0 days.

(21) Appl. No.: 13/432,612

(22) Filed: Mar. 28, 2012

(65) Prior Publication Data
US 2012/0183922 A1 Jul. 19, 2012

Related U.S. Application Data

(63) Continuation of application No. PCT/KR2010/002399, filed on Apr. 16, 2010.

(30) Foreign Application Priority Data

Sep. 30, 2009 (KR) ........................ 10-2009-0093218

(51) Int. Cl.
*A61C 3/00* (2006.01)
(52) U.S. Cl.
USPC ............................................. 433/75; 433/76

(58) Field of Classification Search
USPC .................. 433/75, 76, 173, 174; 606/96–98
See application file for complete search history.

(56) References Cited

U.S. PATENT DOCUMENTS

2002/0192620 A1 12/2002 Jorneus et al.
2006/0121410 A1 6/2006 Aravena
2008/0206714 A1 8/2008 Schmitt

OTHER PUBLICATIONS

International Search Report and Written Opinion of the International Searching Authority; Application No. PCT/KR2010/002399; Issued: Dec. 24, 2010; Mailing Date: Dec. 27, 2010; 7 pages.

*Primary Examiner* — Cris L Rodriguez
*Assistant Examiner* — Eric Rosen
(74) *Attorney, Agent, or Firm* — St. Onge Steward Johnston & Reens LLC (57) ABSTRACT

A guide block for a dental implant procedure, a guide block assembly, and a dental implant procedural technique using the guide block, which enable a dental implant procedure to be accurately performed by allowing one or more surgical holes to be quickly and accurately bored during a boring process in which the one or more surgical holes are bored in an alveolar bone in a dental implant procedure.

9 Claims, 8 Drawing Sheets

GUIDE BLOCK FOR A DENTAL IMPLANT PROCEDURE AND GUIDE BLOCK ASSEMBLY, AND IMPLANT PROCEDURAL TECHNIQUE USING SAME

CROSS-REFERENCE TO RELATED APPLICATIONS

The present application is a continuation of pending International Patent Application PCT/KR2010/002399 filed on Apr. 16, 2010, which designates the United States and claims priority from Korean Patent Application 10-2009-0093218 filed on Sep. 30, 2009, the content of which is incorporated herein by reference.

FIELD OF THE INVENTION

The present invention relates to a guide block for a dental implant procedure, a guide block assembly, and a dental implant procedural technique using the guide block, and more particularly, to a guide block for a dental implant procedure, a guide block assembly, and a dental implant procedural technique using the guide block, which enable a dental implant procedure to be accurately performed and an entire dental implant procedure time to be sharply decreased by allowing one or more surgical holes to be quickly and accurately bored during a boring process in which the one or more surgical holes are bored in an alveolar bone in a dental implant procedure.

BACKGROUND OF THE INVENTION

An implant as a term of dentistry means that an artificially-made tooth is implanted into an alveolar bone of a person. That is, a dental implant procedure indicates an operation that helps a recovery of a tooth function by implanting a tooth root into an alveolar bone in a toothless gum so as to replace a worn-out tooth root, wherein the tooth root is made of a metal material such as titanium that is not rejected by a human body, and then by fixing an artificial tooth thereto.

A common dental prosthesis or a false tooth damages its adjacent teeth and bones according to time. However, an implant is advantageous in that it does not damage its adjacent tooth tissue, has the same shape or function as a natural tooth, does not have a tooth decay, and can be semi-permanently used, so that the implant is widely implanted in recent days.

A dental implant procedure will now be briefly described. The dental implant procedure is performed in a manner that a fixture is implanted and osseointegrated to a surgical hole that is bored in an alveolar bone by using an exclusive-use drill, an abutment is combined with the fixture, and then a final dental prosthesis covers the abutment.

The implant is advantageous in that it recovers a single lost-tooth, increases a function of artificial teeth of a patient having only few teeth or a toothless patient, improves an aesthetic feature of a dental recovery by a dental prosthesis, disperses a heavy load applied to its adjacent alveolar bone tissue, and stabilizes a row of teeth.

In the dental implant procedure, a surgical hole is bored in a patient's alveolar bone by using the exclusive-use drill, and since the implant is implanted into the surgical hole, the boring process of the surgical hole is very important.

In order to bore the surgical hole, first, the gingival of a patient to have the implant is cut so as to expose an alveolar bone.

Then, a position in the exposed alveolar bone to which the implant is to be implanted is determined, and the predetermined position in the exposed alveolar bone is bored by using a boring instrument such as a drill, so that the surgical hole to which the implant is to be implanted is formed.

Afterward, the implant is implanted into the surgical hole and then the gingival is covered, so that the dental implant procedure is complete.

A process of implanting an implant, and manufacturing and loading a dental prosthesis to the implant is called 'immediate loading' that is advantageous in that a toothless state of a patent can be minimized. After a successful treatment with regard to an immediate loading is reported, in case that index cases are correctly selected, the immediate loading treatment is recognized as a safe procedural technique and then is generally considered as a priority treatment. In the past, a screw-retained restoration type dental prosthesis is preferred since it is easy to remove it when required. However, according to agreed opinions, it is necessary to minimize macro-motion in an implant for two months that are the least period for osseointegration so as to make a long-tem use of the implant possible, thus, a cement-retained restoration type dental prosthesis is preferred due to easiness in the prosthesis manufacture. In a case of the cement-retained restoration type dental prosthesis, it is required to form a dental prosthesis on an upper portion of an implant on the same day as a dental implant procedure. Thus, only when implants are implanted in parallel into correct positions, selection of an abutment may be easy, a dental implant procedure may be simplified, and a treatment term can be shortened, and by doing so, a possibility of occurrence of after-implant problems may be minimized. Thus, there is an increasing demand for a means that helps several implants to be implanted in parallel to each other.

SUMMARY OF THE INVENTION

The present invention provides a guide block for a dental implant procedure, a guide block assembly, and a dental implant procedural technique using the guide block, which enable a dental implant procedure to be accurately performed and an entire dental implant procedure time to be sharply decreased by allowing multiple surgical holes to be quickly and accurately bored in parallel to each other during a boring process in which the multiple surgical holes are bored in an alveolar bone in a dental implant procedure.

According to an aspect of the present invention, there is provided a guide block for a dental implant procedure, the guide block including a main body having a through-hole; and a pair of connecting rings extending in one direction from the main body and having round inner peripheral surfaces, wherein projecting ends project from the main body at either end of the through-hole up to a first height, in a plan view shape of the projecting ends, two opposite directions in the plan view shape of four outer peripheral surfaces of the projecting ends are formed in a circular arc having a curvature corresponding to a curvature of the round inner peripheral surface of the connecting ring, and the other outer peripheral surfaces in the other two opposite directions are formed as straight outer peripheral surfaces, the pair of connecting are separate from each other by a distance corresponding to a thickness of the main body, and a thickness of each of the pair of connecting rings are is greater than the first height, and coupling grooves facing each other and having depths corresponding to the first height are formed in the pair of connecting rings.

Rotation limitation prominences may be formed on the main body in a crossing direction with respect to the pair of connecting rings.

Rotation limitation projections may be formed at the rotation limitation prominences, and one or more sawteeth may be formed on outer peripheral surfaces of the pair of connecting rings.

A portion of outer peripheral surfaces of the pair of connecting rings may be straightly cut in a parallel direction to the straight outer peripheral surfaces of the projecting ends.

The through-hole may have a tapered shape whereby a diameter of one end and a diameter of the other end of the through-hole may be different.

A distance between the straight outer peripheral surfaces of the projecting ends may be equal to or less than a width of the coupling grooves.

According to another aspect of the present invention, there is provided a guide block assembly formed by connecting two or more of the guide block, wherein the guide blocks are connected in a manner that the distance between the straight outer peripheral surfaces of the projecting ends of the guide block (a first guide block), and the width of the coupling grooves of the pair of connecting rings of the guide block (a second guide block) are arranged to face each other, the main body of the first guide block is pushed into a gap between the pair of connecting rings of the second guide block, central axes of the round inner peripheral surfaces of the pair of connecting rings of the first guide block are matched with a central axis of an inner peripheral surface of the through-hole of the second guide block, and then the first guide block and the second guide block relatively rotate with respect to their central axes.

According to another aspect of the present invention, there is provided a dental implant procedural technique for boring implant a surgical hole in an alveolar bone by using the guide block, the dental implant procedural technique including operations of disposing at least one guide block at an upper portion of an alveolar bone of a patient to have an implant; and inserting a drill via the inner peripheral surface of the through-hole of the main body of the at least one guide block, and boring a surgical hole to which a fixture is to be inserted and fixed at the alveolar bone.

By using a guide block for a dental implant procedure, a guide block assembly, and a dental implant procedural technique using the guide block according to one or more embodiments of the present invention, advantages as mentioned below may be obtained.

First, in a toothless case or a partial toothless case, surgical holes and their adjacent teeth are parallel to each other, so that implants to be implanted into the surgical holes, respectively, may be parallel to each other.

Second, when positions of surgical holes for implants are set by using a guide block assembly, the implants may be implanted to be exactly symmetrical with respect to a mid line.

Third, in a case where implants are implanted into maxillary and mandibular bones so as to manufacture implant supported overdentures, it is required to implant multiple implants. In this regard, according to the one or more embodiments of the present invention, it is possible to allow the multiple implants to be implanted in parallel to each other, so that it is particularly convenient for a case of implanting the implant supported overdentures.

Fourth, it is possible to implant multiple implants while the multiple implants are parallel to each other and are vertical to an occlusal plane.

Fifth, a necessary gap between implants may be easily maintained.

Sixth, implants having different lengths may be implanted in parallel to each other by using a stop drill.

Seventh, the maximum of three drills may be simultaneously used, and one or two of three drills may be used as guide pins.

DETAILED DESCRIPTION OF THE INVENTION

Hereinafter, the present invention will be described in detail by explaining exemplary embodiments of the invention with reference to the attached drawings.

Figure 1:
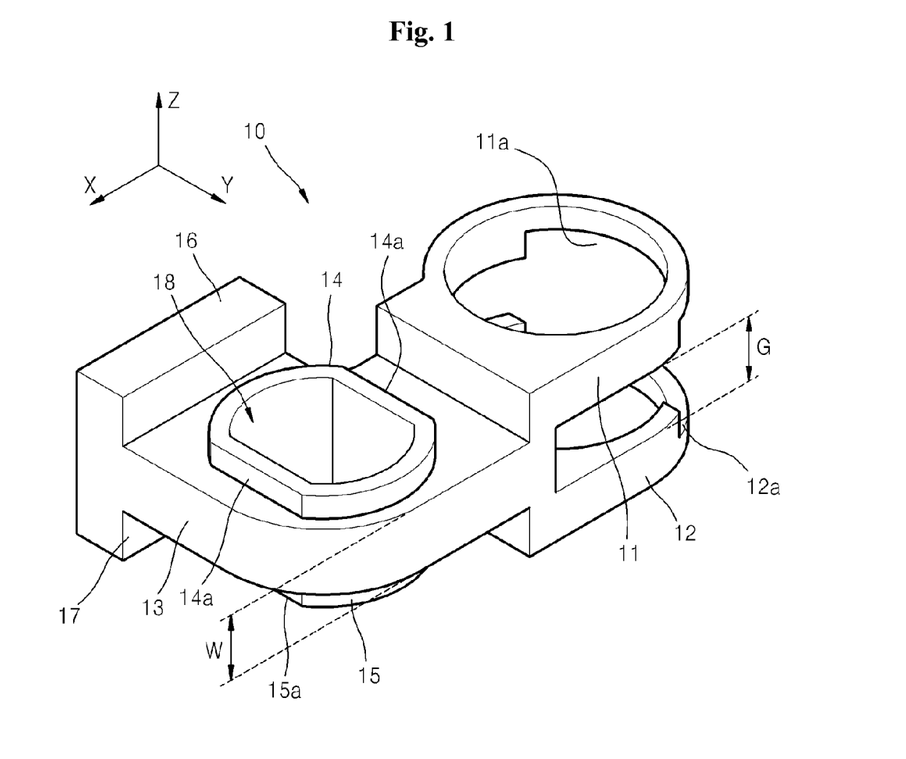
FIG. 1 is a perspective view illustrating a structure of a guide block according to an embodiment 1 of the present invention.
Figure 2:
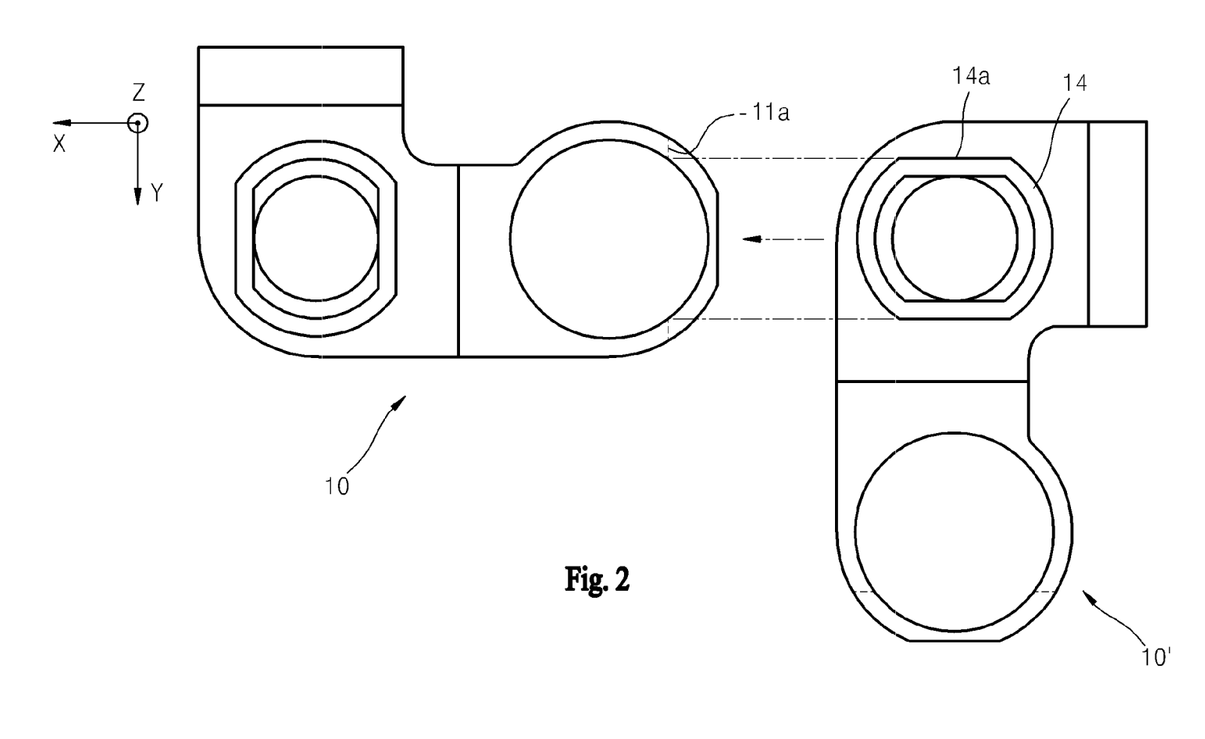
FIG. 2 is a plane view illustrating a method of mutually connecting at least two guide blocks of FIG. 1.
Figure 3:
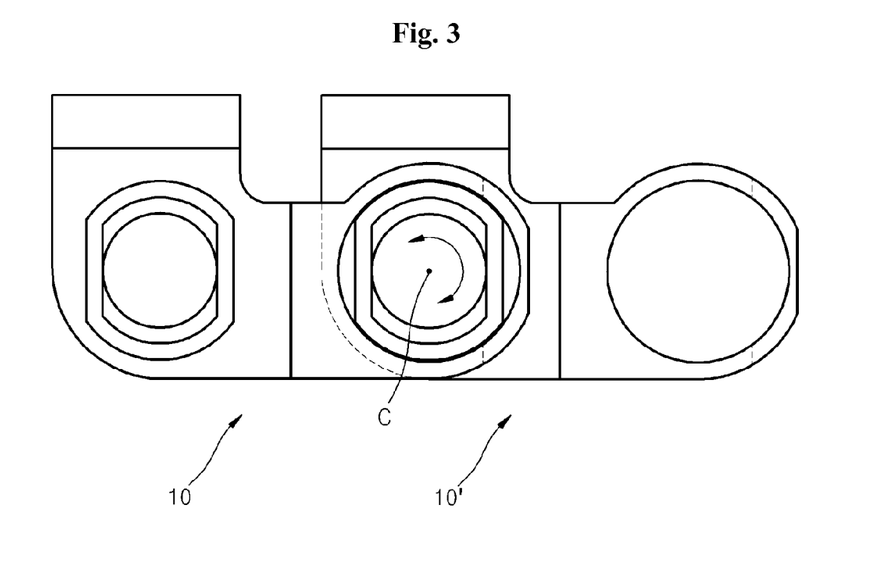
FIG. 3 is a plane view illustrating a status of the two guide blocks that are connected to each other.

FIG. 1 is a perspective view illustrating a structure of a guide block 10 according to an embodiment 1 of the present invention. FIG. 2 is a plane view illustrating a method of mutually connecting at least two guide blocks 10 of FIG. 1. FIG. 3 is a plane view illustrating a status of the two guide blocks 10 that are connected to each other.

As illustrated in FIG. 1, the guide block 10 according to the embodiment 1 includes a main body 13 having a through-hole 18; and a pair of connecting rings 11 and 12 extending in one direction from the main body 13 and having round inner peripheral surfaces.

Projecting ends 14 and 15 project from the main body 13 at either end of the through-hole 18 up to a first height, and a plan view shape of the projecting ends 14 and 15 corresponds to a circle of which both ends are straightly cut. That is, two opposite directions in the plan view shape of four outer peripheral surfaces of the projecting ends 14 and 15 are formed in a circular arc, and the other outer peripheral surfaces in the other two opposite directions are formed as straight outer peripheral surfaces 14a and 15a. Distances between a center of the circular arc and each of straight outer peripheral surfaces 14a and 15a are substantially the same. A curvature of the circular outer peripheral surfaces of the projecting ends 14 and 15 corresponds to a curvature of the peripheral surface of one of the connecting rings 11 and 12. In the present invention, the feature "lengths, widths, gaps, or the like correspond to each other" is not limited to only a complete equality but also include a case in which, according to a machining error and a material, the lengths, the widths, the gaps, or the like may be deformed by a manual power of a user The connecting rings 11 and 12 are separate from each other by a distance G corresponding to a thickness W of the main body 13. The distance G is arranged to allow the main body 13 of another guide block 10 to be inserted between the connecting rings 11 and 12. A thickness of each of the connecting rings 11 and 12 is greater than the first height, and coupling grooves 11a and 12a facing each other and having depths corresponding to the first height are formed in the connecting rings 11 and 12. A distance between the straight outer peripheral surfaces 14a and 15a of the projecting ends 14 and 15 is substantially the same as or less than a width of the coupling grooves 11a and 12a, so as to connect the guide blocks 10.

Rotation limitation prominences 16 and 17 may be formed on the main body 13 in a crossing direction with respect to the connecting rings 11 and 12. In a case where a plurality of the guide blocks 10 are connected to form a guide block assembly, the guide block assembly may be formed to make a circular arc (refer to FIG. 7) that corresponds to a shape of an upper portion of an alveolar bone of a human maxillary bone. In order to make array the guide block assembly having the circular arc shape, it is necessary that rotation can be possible among the guide blocks 10 that form the guide block assembly. However, the guide blocks 10 do not need to rotate by 360°, in consideration of a shape of the maxillary bone, and thus, if a rotation angle is limited to some extent, it is more convenient to match and adjust a shape of the guide block assembly to the shape of the maxillary bone of each patient.

Referring to FIGS. 1 through 3, a longitudinal direction of the rotation limitation prominences 16 and 17 and a direction of the straight outer peripheral surfaces 14a and 15a of the projecting ends 14 and 15 are substantially perpendicular to each other, and the longitudinal direction of the rotation limitation prominences 16 and 17 and a disposition direction of the through-hole 18 are substantially perpendicular to each other with respect to a center point of the through-hole 18, but one or more embodiments of the present invention are not limited to the perpendicular direction. However, as illustrated in FIGS. 1 through 3, if the aforementioned elements are made to be perpendicular to each other, it is easy to manufacture and connect them.

The guide blocks 10 and 10' having the aforementioned structure may be connected to each other in a manner shown in FIG. 2. As illustrated in FIG. 2, the coupling grooves 11a and 12a of the first guide block 10, and the projecting ends 14 and 15 of the second guide block 10' are disposed to face each other. Next, the main body 13 of the second guide block 10' is pushed into a gap between the connecting rings 11 and 12 of the first guide block 10 in an arrow direction of FIG. 2, and then a central axis of the inner peripheral surface of the connecting ring 11 of the first guide block 10 is matched with a central axis of an inner peripheral surface of the through-hole 18 of the second guide block 10'. Afterward, by relatively rotating the first guide block 10 and the second guide block 10' with respect to the central axes, connection is completed. A complete connection status is shown in FIG. 3, and as illustrated in an arrow of FIG. 3, relative rotation around a central axis C is possible.

Figure 4:
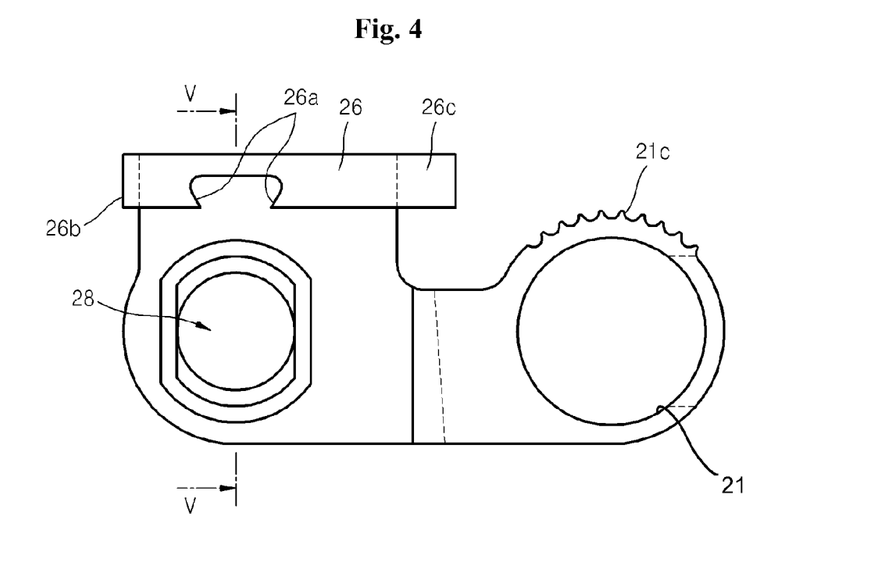
FIG. 4 is a perspective view illustrating a structure of a guide block according to an embodiment 2 of the present invention.
Figure 5:
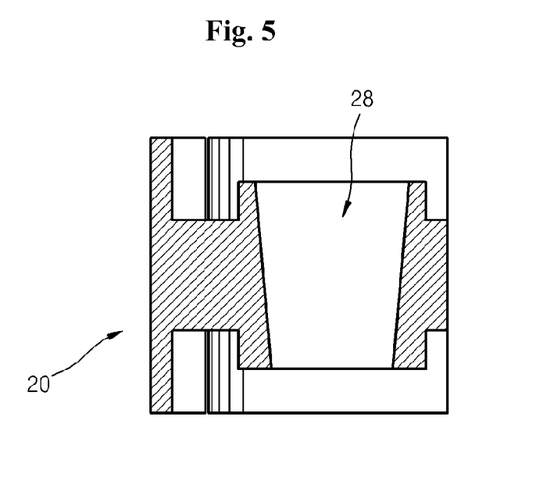
FIG. 5 is a cross-sectional view of the guide block, taken along a line V-V of FIG. 4 and illustrating a cross-sectional shape of a through-hole of the guide block.
Figure 6:
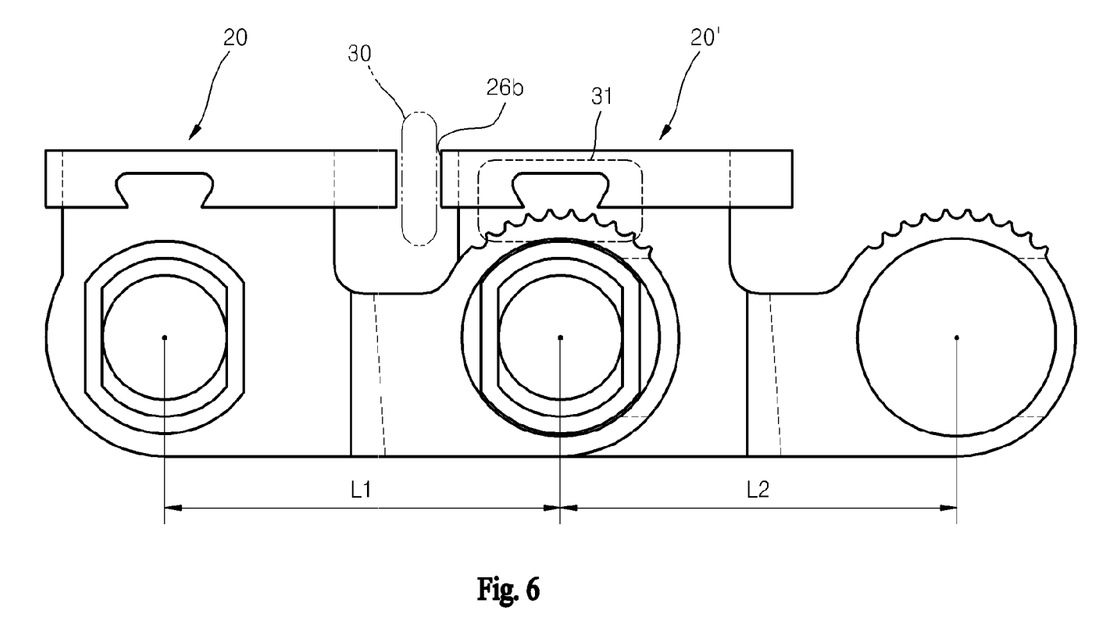
FIG. 6 illustrates a status of the two guide blocks shown in FIG. 4 and connected to each other.

FIG. 4 is a perspective view illustrating a structure of a guide block 20 according to an embodiment 2 of the present invention. FIG. 5 is a cross-sectional view of the guide block 20, taken along a line V-V of FIG. 4 and illustrating a cross-sectional shape of a through-hole 28 of the guide block 20. FIG. 6 illustrates a status of the two guide blocks 20 shown in FIG. 4 and connected to each other.

As illustrated in FIGS. 4 through 6, the guide block 20 of the embodiment 2 is different from the guide block 10 of the embodiment 1 in that sawteeth 21c are formed on an outer peripheral surface of a connecting ring 21, a rotation limitation projection 26a is formed at a rotation limitation prominence 26, and rotation limitation prominence projecting portions 26b and 26c are formed at ends of the rotation limitation prominence 26.

The sawteeth 21c and the rotation limitation projection 26a function to facilitate adjustment of a relative rotation angle in a status in which the guide blocks 20 and 20' are connected to each other. Rotation of the sawteeth 21c may be limited by the rotation limitation projection 26a, and the relative rotation angle between the guide blocks 20 and 20' may be adjusted by the pitch of the sawteeth 21c so that the relative rotation angle between the guide blocks 20 and 20' is easily adjusted.

The guide block according to the one or more embodiments of the present invention may be formed of a metal material such as aluminum, brass, or the like, or may be formed of a polymer resin. In a case of the embodiment 2, it is necessary for the sawteeth 21c and the rotation limitation projection 26a to be slightly deformed while they are bumped into each other, so that it may be more advantageous if the guide block 20 is formed of a polymer resin. However, in order to effectively guide a drill, the guide block 20 may be formed of a material having predetermined hardness.

The feature in which the rotation limitation prominence projecting portions 26b and 26c are formed at the ends of the rotation limitation prominence 26 is used when a guide block assembly is formed according to a streamline of a maxillary bone, by connecting a plurality of the guide blocks 20. For example, for a patient having a small maxillary bone, a curvature of the streamline of the guide block assembly has to be increased, and to do so, an angle between the adjacent guide blocks 20 has to be increased. In this case, if necessary, an end of the rotation limitation prominence 26 may be cut, so that a relative angle between the guide blocks 20 may be increased. In an opposite case, a resin 30 may be inserted into a gap between the rotation limitation prominences 26 of the adjacent guide blocks 20, so that an angle between the adjacent guide blocks 20 may be decreased. Also, a resin 31 may cover a portion where the sawteeth 21c meets the rotation limitation projection 26a, and by doing so, rotation among the connected guide blocks 20 may be adjusted. Although the aforementioned features are shown in FIGS. 4 through 6 illustrating the embodiment 2, the aforementioned features may also be applied to the embodiment 1.

As shown in the cross-sectional view of FIG. 5, a cross-sectional shape of an inner peripheral surface of the through-hole 28 is tapered. That is, the through-hole 28 has a tapered shape so that a diameter of one end and a diameter of the other end of the through-hole 28 are different, and a central axis of the through-hole 28 is parallel with a longitudinal direction of the through-hole 28. Since a shape of a human jaw is not rectangular but is streamlined, by doing so, drilling may be performed toward a center of a maxillary bone. Although the feature of the tapered inner peripheral surface of the through-hole 28 is described with reference to the embodiment 2, the feature may also be applied to the embodiment 1 and is actually shown in FIGS. 2 and 3.

The plurality of the guide blocks 20 may be manufactured in such a manner that distances between central points of the connecting rings 21a, and distances between central points of the through-hole 28 are different. FIG. 6 shows distances L1 and L2 between central points of the connected two guide blocks 20. Distances between teeth may be different in every person, and even in the same person, distances between teeth in a molar-teeth portion and a front-teeth portion may be different. Thus, in order to prepare the distances, several guide blocks in which distances between central points are different, e.g., 5 mm, 6 mm, 7 mm, and the like are manufactured and then are assembled to match with distances between target teeth positions, so that a guide block assembly may be formed. Also, in a case where implant target positions are not adjacent but are distant from each other, a guide block assembly may be formed by connecting several guide blocks and then may be applied thereto. Accordingly, distant implants may be implanted into an alveolar bone while they are parallel to each other.

Figure 7:
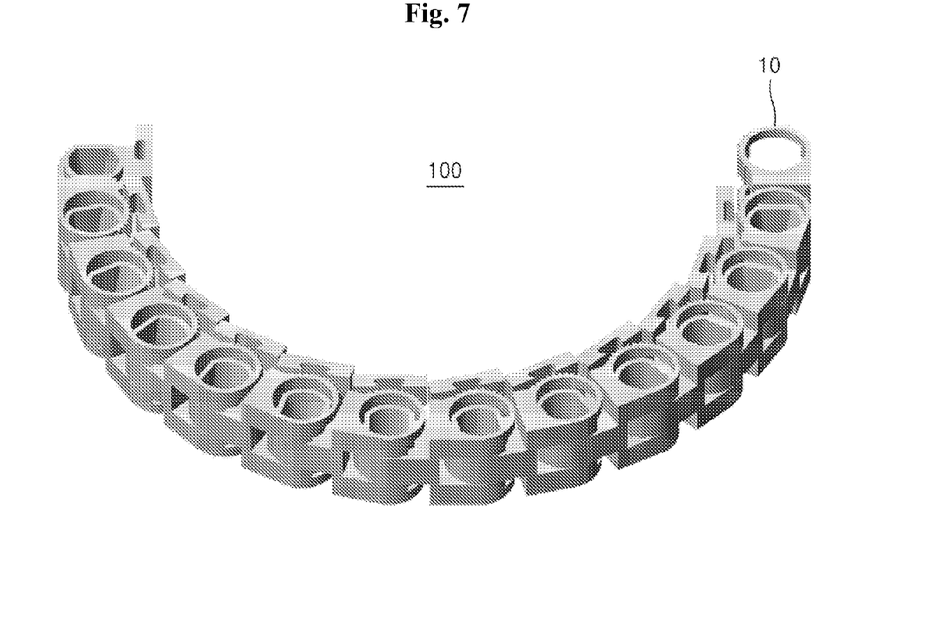
FIG. 7 illustrates a guide block assembly that is formed by connecting the guide blocks of the embodiment 2 and that is for a toothless case.
Figure 8:
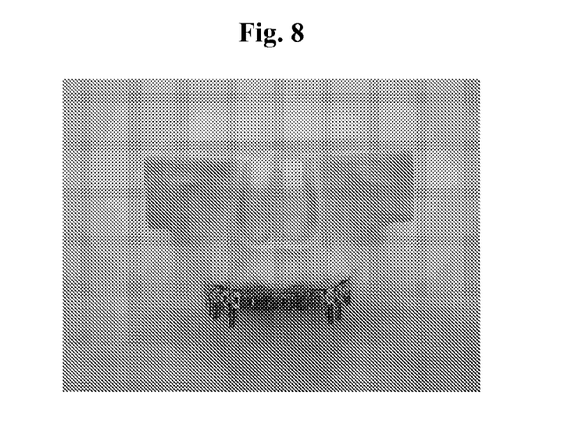
FIG. 8 is an image showing a case in which the guide block assembly of FIG. 7 for the toothless case is combined with a maxillary model.

FIG. 7 illustrates a guide block assembly 100 that is formed by connecting the guide blocks 10 of the embodiment 2 and that is for a toothless case. FIG. 8 is an image showing a case in which the guide block assembly 100 of FIG. 7 for the toothless case is combined with a maxillary model, and FIG. 9 is an image showing a reverse state of the combination of the guide block assembly 100 and the maxillary model of FIG. 8.

Figure 9:
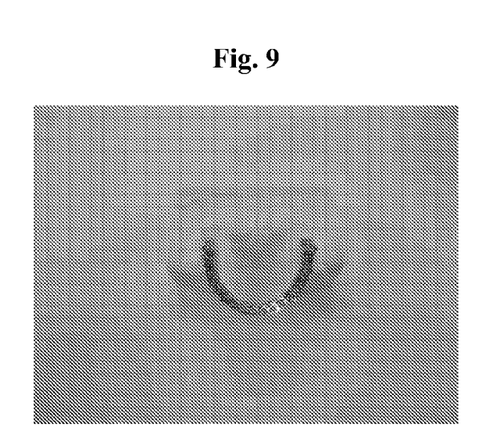
FIG. 9 is an image showing a reverse state of the combination of the guide block assembly and the maxillary model of FIG. 8.

As illustrated in FIGS. 7 through 9, in the toothless case, the guide block assembly 100 may be formed by connecting the guide blocks 10 so as to match with shapes of teeth, and then may be fixed into an alveolar bone by using parallel pins.

Figure 10:
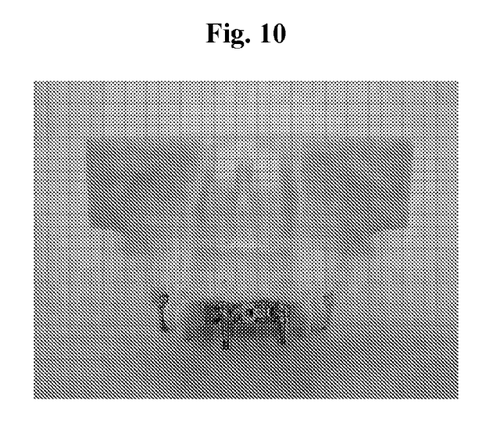
FIG. 10 is an image showing a case in which the guide block according to the one or more embodiments is used in implanting a plurality of implants into a portion of a maxillary bone.
Figure 11:
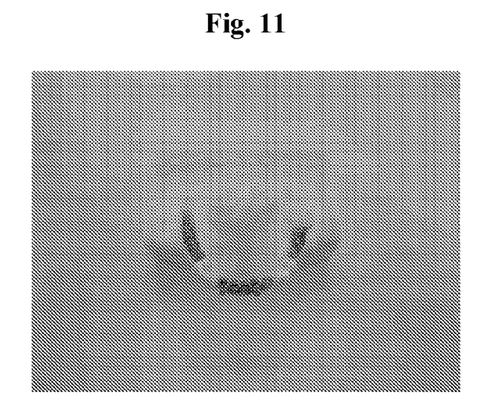
FIG. 11 is an image showing a reverse state of a model shown in FIG. 10.

FIG. 10 is an image showing a case in which the guide block according to the one or more embodiments is used in implanting a plurality of implants into a portion of a maxillary bone. FIG. 11 is an image showing a reverse state of a model shown in FIG. 10.

As illustrated in FIGS. 10 and 11, for a partial toothless case, the number of the guide blocks is adjusted so as to correspond to a distance between teeth. Then, the guide blocks are connected and fixed into a toothless portion.

By using the guide block having the aforementioned structure, surgical holes may be bored in a manner below.

First, one or more guide blocks are connected and then disposed at upper portions of alveolar bones of a patient to have implants. Next, the surgical holes via which fixtures are to be inserted and fixed into the alveolar bones are bored by inserting a drill via the inner peripheral surfaces of the through-holes of the main bodies of the guide blocks. When holes to fix the guide block assembly at the alveolar bones are bored by using parallel pins or guide pins, a drill to bore the holes may be inserted via the through-holes of the guide block assembly.

While this invention has been particularly shown and described with reference to exemplary embodiments thereof, it will be understood by those of ordinary skill in the art that various changes in form and details may be made therein without departing from the spirit and scope of the invention as defined by the appended claims. The exemplary embodiments should be considered in a descriptive sense only and not for purposes of limitation. Therefore, the scope of the invention is defined not by the detailed description of the invention but by the appended claims, and all differences within the scope will be construed as being included in the present invention.

What is claimed is:

1. A guide block for a dental implant procedure, the guide block comprising:
   a main body having a through-hole; and
   a pair of connecting rings extending in one direction from the main body, the pair of connecting rings having round inner peripheral surfaces,
   wherein projecting ends project from the main body at opposite ends of the through-hole up to a first height,
   wherein each of the projecting ends comprises four outer peripheral surfaces; and
   wherein in a plan view shape of each of the projecting ends, two opposite surfaces of the four outer peripheral surfaces of the projecting ends are formed in a circular arc having a curvature corresponding to a curvature of the round inner peripheral surfaces of the connecting rings, and two other outer peripheral surfaces of the four outer peripheral surfaces are formed as straight outer peripheral surfaces,
   wherein the pair of connecting rings are separated from each other by a distance corresponding to a thickness of the main body, and a thickness of each of the pair of connecting rings is greater than the first height, and
   wherein the pair of connecting rings have coupling grooves facing each other and having depths corresponding to the first height.

2. The guide block of claim 1, wherein rotation limitation prominences are formed on the main body in a crossing direction with respect to the pair of connecting rings.

3. The guide block of claim 2, wherein rotation limitation projections are formed at the rotation limitation prominences, and
   one or more sawteeth are formed on outer peripheral surfaces of the pair of connecting rings.

4. The guide block of claim 2, wherein each of the rotation limitation prominences has projecting portions that project from the main body while the projecting portions extend in a longitudinal direction of the rotation limitation prominences.

5. The guide block of claim 1, wherein a portion of outer peripheral surfaces of the pair of connecting rings is straightly cut in a parallel direction to the straight outer peripheral surfaces of the projecting ends.

6. The guide block of claim 1, wherein the through-hole has a tapered shape whereby a diameter of one end and a diameter of the other end of the through-hole are different.

7. The guide block of claim 1, wherein a distance between the straight outer peripheral surfaces of the projecting ends is equal to or less than a width of the coupling grooves.

8. A guide block assembly formed by connecting two or more of the guide block of claim 1,
   wherein the two or more guide blocks are connected in a manner that the distance between the straight outer peripheral surfaces of the projecting ends of a first guide block of the two or more guide blocks, and the width of the coupling grooves of the pair of connecting rings of a second guide block of the two or more guide blocks are arranged to face each other,
   wherein the main body of the first guide block is pushed into a gap between the pair of connecting rings of the second guide block,
   wherein a central axes of the round inner peripheral surfaces of the pair of connecting rings of the first guide block are matched with a central axis of an inner peripheral surface of the through-hole of the second guide block, and
   wherein the first guide block and the second guide block rotate relatively with respect to their central axes.

9. A dental implant procedural technique for boring a surgical hole in an alveolar bone by using at least one guide block of claim 1, the dental implant procedural technique comprising:
   disposing the at least one guide block of claim 1 at an upper portion of an alveolar bone of a patient; and inserting a drill via the inner peripheral surface of the through-hole of the main body of the at least one guide block, and boring a surgical hole to which a fixture is to be inserted and fixed at the alveolar bone.

* * * * *